(12) United States Patent
Gandelheid et al.

(10) Patent No.: US 6,736,975 B2
(45) Date of Patent: May 18, 2004

(54) METHOD OF SEPARATING COMPOUND(S) FROM MIXTURE(S)

(75) Inventors: Thierry Gandelheid, Chapel Hill, NC (US); James Edward Fayson, Jr., Raleigh, NC (US)

(73) Assignee: Scynexis, Inc., Durham, NC (US)

( * ) Notice: Subject to any disclaimer, the term of this patent is extended or adjusted under 35 U.S.C. 154(b) by 0 days.

(21) Appl. No.: 09/998,137

(22) Filed: Dec. 3, 2001

(65) Prior Publication Data

US 2003/0102265 A1 Jun. 5, 2003

(51) Int. Cl.$^7$ .............................................. B01D 15/08
(52) U.S. Cl. ..................... 210/659; 210/656; 210/198.2
(58) Field of Search ................................ 210/635, 656, 210/659, 143, 198.2; 436/161

(56) References Cited

U.S. PATENT DOCUMENTS

| | | | |
|---|---|---|---|
| 5,350,520 A | 9/1994 | Kikumoto | 210/656 |
| 5,398,539 A | 3/1995 | Gordon et al. | 73/23.35 |
| 5,670,054 A | 9/1997 | Kibbey et al. | 210/656 |
| 5,670,379 A | 9/1997 | Ito et al. | 436/161 |
| 5,766,481 A | 6/1998 | Zambias et al. | 210/656 |
| 6,309,541 B1 | 10/2001 | Maiefski et al. | 210/198.2 |
| 6,344,172 B1 * | 2/2002 | Afeyan | 210/656 |
| 6,413,431 B1 | 7/2002 | Abedi | 210/656 |
| 2002/0023878 A1 | 2/2002 | Collins et al. | 210/198.2 |

FOREIGN PATENT DOCUMENTS

WO    WO 01 90739 A1    11/2001    .................. 210/656

OTHER PUBLICATIONS

Roth, H.J., et al., "One Sample—One Fraction Purification of Compound Libraries Without Online MS Detection", New Chemical Technologies Accelerating Drug Discovery; Mar. 29–30, 2001; San Diego, CA.

* cited by examiner

Primary Examiner—Ernest G. Therkorn
(74) Attorney, Agent, or Firm—Burns, Doane, Swecker & Mathis, L.L.P.

(57) ABSTRACT

The invention relates to methods of separating compounds of interest from mixtures using high performance liquid chromatography (HPLC). An initial separation of a sample of a mixture is performed to predict a retention time and elution time for the compound of interest on a preparative scale HPLC column and, optionally, to verify that an expected compound of interest is present in the mixture. Preparative scale HPLC is then used to separate and collect at least a portion of the compound from the mixture using the predicted elution time of the compound.

23 Claims, 3 Drawing Sheets

CORRELATION FUNCTION

METHOD OF SEPARATING COMPOUND(S) FROM MIXTURE(S)

FIELD OF THE INVENTION

The present invention relates to the separation of a compound or compounds of interest from a mixture or mixtures using high performance liquid chromatography.

BACKGROUND OF THE INVENTION

Various methods for identifying and separating reaction products from mixtures are known. These methods are important to the formation of purified libraries of compounds produced by combinatorial chemistry.

U.S. Pat. No. 5,670,054 teaches an automated high performance liquid chromatography (HPLC) system that separates, identifies, purifies, and quantitates complex mixtures of reaction products or natural products on a semi-preparative or preparative scale. The patent teaches generating and digitally storing a chromatogram from a first HPLC column along with mass spectrometric data to guide sample purification on a semi-preparative or preparative HPLC system.

There is a need for a method of separating reaction products from mixtures that does not rely on electronically stored UV chromatographic data and mass spectrometric data to guide a preparative HPLC system.

SUMMARY OF THE INVENTION

The present invention relates to separating compounds of interest from mixtures using high performance liquid chromatography (HPLC). According to one aspect of the present invention, a method of separating a compound of interest from a mixture is provided that comprises the steps of: (a) providing a mixture containing a compound of interest, the compound of interest having an expected mass; (b) subjecting a portion of the mixture to a separation using an analytical HPLC column to produce an eluate stream; (c) analyzing the eluate stream using a mass spectrometer to determine a retention time of the compound of interest on the analytical HPLC column; (d) predicting an elution time for the compound of interest from a preparative scale HPLC column using the determined retention time of the compound of interest on the analytical HPLC column; (e) subjecting all or a portion of the remaining mixture to a preparative scale HPLC system comprising a preparative scale HPLC column; and (f) collecting at least a portion of the compound of interest using the predicted elution time.

In one embodiment, the elution time for the compound of interest is predicted by: (1) predicting a retention time of the compound of interest from the preparative scale HPLC column using a predetermined correlation function between the analytical HPLC column and the preparative scale HPLC column along with the determined retention time of the compound on the analytical HPLC column; and (2) selecting a window of time around the predicted retention time within which the compound is expected to elute. In another embodiment, a dynamic correlation function is used to predict the elution time for the compound of interest. In a further embodiment, the elution time for the compound of interest is predicted using an artificial neural network.

According to another aspect of the present invention, a method of separating compounds of interest present in a plurality of reaction product mixtures is provided. The method comprises the steps of: (a) providing a plurality of reaction product mixtures, each mixture expected to contain a compound of interest having an expected mass; (b) separately subjecting a portion of each reaction product mixture to a separation using an analytical HPLC column to produce a plurality of eluate streams; (c) analyzing each eluate stream using a mass spectrometer to verify that the eluate stream contains a compound with an expected mass and to determine a retention time of each compound with an expected mass on the analytical HPLC column; (d) predicting an elution time for each compound with an expected mass from a preparative scale HPLC column using the determined retention time for each compound with an expected mass on the analytical HPLC column; (e) separately subjecting all or a portion of each remaining mixture verified to contain a compound with the expected mass to a preparative scale HPLC system comprising a preparative scale HPLC column and a fraction collector; and (f) separately collecting at least a portion of each compound verified to be present with the fraction collector using the predicted elution time for each compound.

In one embodiment, at least two eluate streams produced in step (b) are combined for analysis in step (c) in a common mass spectrometer. The at least two eluate streams are chosen such that the expected compounds of interest in the streams have different expected masses that are distinguishable by mass spectrometry.

In another embodiment, at least two eluate streams produced in step (b) are combined for analysis in step (c) in a common mass spectrometer. At least one of the eluate streams is mechanically coded such that the expected compounds of interest in the streams are distinguishable by mass spectrometry.

According to yet another aspect of the present invention, a method of separating a compound of interest from a mixture is provided that comprises the steps of: (a) providing a mixture containing a compound of interest; (b) subjecting a portion of the mixture to a separation using thin layer chromatography to determine an Rf value for the compound of interest; (c) predicting an elution time of the compound of interest on a preparative scale HPLC column using the determined Rf value for the compound of interest; (d) subjecting all or a portion of the remaining mixture to a preparative scale HPLC system comprising a preparative scale HPLC column; and (e) collecting at least a portion of the compound of interest using the predicted elution time.

DETAILED DESCRIPTION OF THE INVENTION

Figure 1:
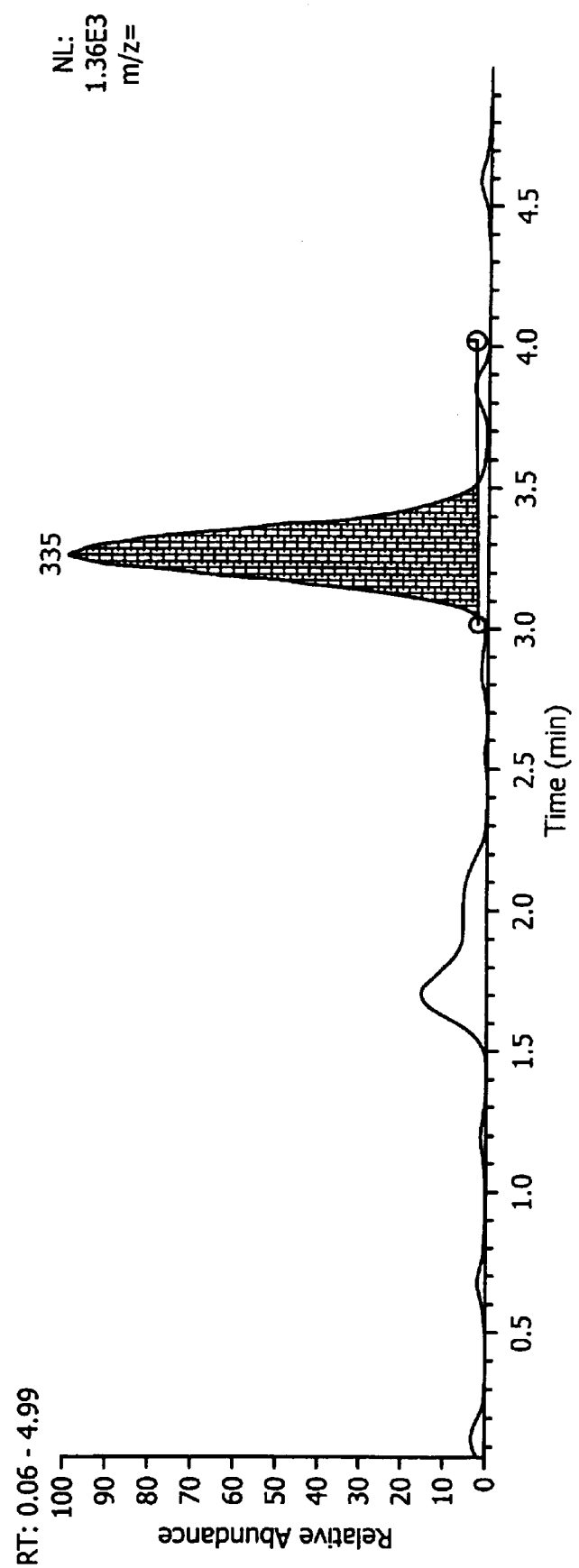
FIG. 1 illustrates a mass chromatogram (obtained according to Example 1) of elution time versus relative abundance of the mass to charge ratio 335.

According to the present invention, a method is provided for separating one or more compounds of interest from one or more mixtures. The invention involves an initial separation of a sample of the mixture to predict a retention time for the compound on a preparative scale HPLC column and, optionally, to verify that an expected compound of interest is present in the mixture. The initial separation may be performed using thin layer chromatography (TLC) or by using analytical high performance liquid chromatography coupled with mass spectrometry (HPLC-MS). Preparative scale HPLC is then used to separate and collect the compound(s) from the mixture(s).

Unless otherwise stated, the following terms used in the specification and claims have the meanings given below:

"Analytical high performance liquid chromatography (HPLC)" means an HPLC system which is capable of producing fractions in the nanogram to low microgram range. Typical analytical HPLC systems of the present invention include a column packed with a suitable stationary phase, a suitable mobile phase, and a pump or pumps for forcing the mobile phase through the column. The mobile phase may be supplied isocratically or by gradient.

"Preparative scale HPLC" means an HPLC system which is capable of producing high microgram, milligram, or gram sized product fractions, and includes both preparative and semi-preparative columns, but does not include analytical HPLC columns. Typical preparative scale HPLC systems of the present invention include a column packed with a suitable stationary phase, a suitable mobile phase, and a pump or pumps for forcing the mobile phase through the column. The mobile phase may be supplied isocratically or by gradient.

"Retention time" of a specific component or compound means the time elapsed between the time of sample introduction and the time of the appearance of a peak maximum for that component or compound.

"Predicted elution time" means a period or "window" of time around a predicted retention time of a compound or component on a preparative scale HPLC column within which the compound or component is expected to elute.

"Reaction product mixture" means a mixture formed by combining reactants that are expected to produce a particular reaction product (i.e., an expected compound of interest). The reaction product mixture may include the expected compound, other reaction products, and/or reagents.

"Expected compound" means a compound expected to be present in a mixture.

"Expected mass" means the predicted molecular weight of an expected compound.

"Chromatogram" means a record obtained by chromatography which is a plot of a detector signal output versus time or elution volume.

"HPLC compatible detector" means a detector suitable for use in an HPLC system which is capable of providing a detectable signal upon elution of a compound peak. A detector capable of generating a signal when a compound elutes from the column is an HPLC compatible detector. A detector capable of detecting a desired component is not an "incompatible" detector due to its inability to detect a non-desired peak.

"Artificial neural network" means a mathematical system designed to operate in the way a biological nervous system operates. That is, the network can learn, memorize, and create relationships amongst data. The neural network is comprised of a processing system with multiple interconnected processing units that are linked together with weighted connections.

According to the invention, one or more mixtures are provided that are each expected to contain a compound of interest with an expected mass. The mixture or mixtures may be reaction product mixture(s) and may be provided, for example, by combinatorial chemistry aimed at providing a library of compounds. A portion of each mixture is subjected to a separation to predict a retention time of the compound of interest on a preparative scale HPLC column and, optionally, to verify that the compound or compounds of interest are in the sample.

In one aspect of the present invention, a portion of each mixture is separately subjected to a separation using an analytical HPLC system to produce an eluate stream. The separation is used to determine the retention time of the compound of interest, which is used to predict the retention time of the compound of interest on the preparative scale HPLC as further discussed below. Each sample is separately introduced onto an analytical HPLC column and mobile phase is supplied isocratically or by gradient to the column by a pump or pumps. Any analytical HPLC system that is compatible with a particular mixture and that is useful in separating the compound of interest from the mixture may be used with the present invention. The components of the HPLC system (such as, for example, the column, the stationary phase, and the mobile phase) and the conditions used with the system (such as, for example, pressure and flow rate) may vary with the particular compound and mixture to be introduced into the system.

In one embodiment, each of the eluate streams are passed through an HPLC compatible detector such as, for example, a UV detector, to determine whether or not the desired compound is pure enough to bypass a separation/purification step (i.e., a separation using a preparative scale HPLC column). If the desired compound does not require further purification, the remaining mixture containing the compound bypasses the purification step. If the desired compound is not present in a pure enough form, the mixture containing the compound is subjected to the purification step, more fully discussed below.

Each of the one or more eluate streams from the analytical HPLC is analyzed using a mass spectrometer to verify that the eluate stream (and therefore that the original mixture) contains a compound with the expected mass. If a compound with an expected mass for a specified eluate stream is detected, the mass spectrometer is used to determine a retention time of the compound on the analytical HPLC column. The mass spectrometer may be configured so that the only data collected is the expected mass of the compound or compounds of interest and the retention time of the compound or compounds on the analytical HPLC column. If the expected mass of a compound of interest is not detected, the mixture expected to contain the compound of interest is not subjected to the separation step using preparative scale HPLC. Any mass spectrometer that is compatible with a particular mixture and that is useful in detecting the expected mass of the compound of interest may be used with the present invention.

In one embodiment, a portion of each of a plurality of mixtures is separately subjected to analytical HPLC to produce a plurality of eluate streams. At least two of the plurality of eluate streams from the analytical HPLC columns may be combined for analysis in a common mass spectrometer. Other eluate streams may also be combined and fed to the same or a different mass spectrometer. The streams that are combined may be chosen such that each expected compound of interest has a different expected mass that is distinguishable by mass spectrometry from the mass of the compound(s) of interest in the other stream(s). Streams that have the same or similar masses may also be combined for analysis in a common mass spectrometer so long as the streams are coded such that the peaks on the mass spectrometer are distinguishable from each other. Such streams could be coded using mechanical means. For example, mechanical band broadening could be used to distinguish two peaks having the same mass. That is, by broadening one of the two peaks having the same mass, the peaks could be distinguished by mass spectrometry and correlated with the mixture from which it originated. A compound peak eluting from one HPLC column could be broadened with respect to a compound peak from another HPLC column by various methods, such as, for example, using wider tubing on one HPLC column, using a longer length of tubing on one column, or using a connector on one column with a larger dead volume. These methods ensure extra solvent is mixed with the compound eluting from one HPLC column as compared to the peak from the other HPLC column, thus broadening the peak from that column as compared to the peak from the other column.

In another aspect of the present invention, a portion of each mixture is subjected to a separation using thin layer chromatography (TLC) to produce one or more spots or zones. Using the results of the TLC, the Rf value of each compound of interest is determined and is used to predict the retention time of the compound of interest on the preparative scale HPLC column as further described below. The TLC may be used to verify that an expected compound of interest is present in the original mixture by, for example, spotting the expected compound next to the sample, co-spotting the expected compound and the sample, performing multiple TLCs using varying solvents or solvent mixtures, and/or performing a two-dimensional TLC. In addition, the TLC may be coupled with mass spectrometry (TLC-MS) in order to identify the spot or zone containing the compound of interest to determine the correct Rf of the compound of interest and/or to verify that the compound of interest is present in the sample. TLC-MS may be performed, for example, by removing the spot or zone from the TLC plate and then placing the spot or zone in solvent to perform mass spectrometry or by performing mass spectrometry directly on the TLC plate for one or more spots or zones (e.g., by moving the spot or zone through the ion source of the mass spectrometer).

After the initial separation using analytical HPLC or TLC, an elution time from a preparative scale HPLC column is predicted for the compound or compounds present in the mixture or mixtures based on the initial separation. The elution time of a particular compound is predicted using the determined retention time for the compound on the analytical HPLC column or using the Rf for the compound determined using the TLC. The elution time is predicted by first predicting the retention time of the compound on the preparative scale HPLC column and then selecting a "window" of time around the predicted retention time on the preparative scale HPLC column within which the compound is expected to elute. The retention and elution times on a preparative scale HPLC column may be predicted using different methods.

One method of predicting the elution time involves predicting the retention time using a "correlation function." The "correlation function" may be a correlation (linear or otherwise) of retention time on an analytical HPLC column (with specified components) versus retention time on a preparative scale HPLC column (with specified components). Two or more test compounds can be used to determine the correlation function between an analytical HPLC column and a preparative scale HPLC column by determining each test compound's retention time on each column. Preferably, a range of polar and non-polar test compounds are used to determine the correlation function. For example, the following set of compounds could be used to determine the correlation function: acetophenone, benzene, toluene, ethyl paraben, propyl paraben, and 2,6-dimethylnaphthalene. However, it should be noted that other sets of compounds may be used in the present invention that have or do not have ranges of different properties.

In a like manner, the retention time of a compound on a preparative scale HPLC column could be determined using a "correlation function" that is a correlation (linear or otherwise) of Rf values from TLC (with specified components) versus retention time on a preparative scale HPLC column (with specified components). Two or more test compounds could be used to determine the correlation function between the TLC and a preparative scale HPLC column by determining each test compound's Rf on the TLC and each test compound's retention time on the preparative scale HPLC column.

After predicting the retention time of the compound on the preparative scale HPLC column, the elution time is predicted. The elution time is predicted using a "window" of time around the predicted retention time. That is, a period of time before and after the predicted retention time is selected that is expected to collect at least some, and preferably all or most of the compound of interest. The window preferably is of sufficient time such that all or a majority of the compound of interest elutes therein. If the window of time is too small, all of the compound of interest will not be collected. If the window of time is too large, other components may be collected with the compound of interest and the value of the separation may be diminished. The predicted elution time may include extra time to compensate for error that may be present in the predicted retention time based on the correlation factor between the analytical HPLC (or the TLC) and the preparative scale HPLC. The actual length of time selected for the window may be guided by a number of parameters, including the average peak width of a compound from an analytical HPLC column (obtained, e.g., by a UV detector or mass spectrometer), the diameter of a compound spot from TLC, and/or HPLC factors such as flow rate and amount of sample.

In addition to using a static correlation function (e.g., a linear correlation function), a dynamic correlation of the analytical HPLC data (or the TLC data) to the retention/elution time of the compound of interest on the preparative scale HPLC could be used. That is, factors that are not constant (e.g., changes in the column over the column life, temperature, etc.) could be taken into account in the prediction. In addition, changes to factors that are constant in a static correlation (e.g., flow rate, mobile phase, column size, etc.) could be accounted for in a dynamic correlation. Using such a dynamic correlation, the retention and elution times of the compound of interest could be predetermined by varying the parameters of the preparative scale HPLC. Furthermore, the components and/or conditions used during the preparative scale HPLC (e.g., flow rate, mobile phase, etc.) could be changed to gain the best separation of a compound from a mixture while still being able to predict the retention and elution times.

An artificial neural network could also be used to predict the retention and elution times. Unlike a linear correlation function, a neural network is capable of predicting the retention time of a compound on a preparative scale HPLC column based on a retention time on an analytical HPLC column or based on an Rf from a TLC in a non-linear and dynamic fashion. A neural network may even be able to choose different components and/or conditions to be used in the preparative scale HPLC in order to gain the best separation of a compound from a mixture.

Each remaining mixture or mixtures (or a portion thereof) are then separately subjected to a separation using a preparative scale HPLC system to produce an eluate stream. Preferably, only the mixture or mixtures verified to contain an expected compound of interest are subjected to the separation on the preparative scale HPLC system. The preparative scale HPLC system includes a preparative scale HPLC column and preferably includes a fraction collector. Each sample is introduced onto the preparative scale HPLC column and mobile phase is supplied isocratically or by gradient to the column by a pump or pumps. Any preparative scale HPLC system that is compatible with a particular mixture and that is useful in separating a compound of interest from the mixture may be used with the present invention. The components of the HPLC system (such as, for example, the column, the stationary phase, and the mobile phase) and the conditions used with the system (such as, for example, pressure and flow rate) may vary with the particular compound and mixture to be introduced into the system.

The preparative scale HPLC system may also include one or more HPLC compatible detectors. Examples of detectors that may be used include UV detectors, evaporative light scattering detectors (ELSD), refractive index detectors (for isocratic methods), and chemiluminescent nitrogen detectors. It is noted, however, that no HPLC compatible detector is required to be present in or used with the preparative scale HPLC system in the methods of the present invention, and in one aspect of the invention no detectors are used with the preparative scale HPLC.

During each separation, the compound (or a portion of the compound) of interest is collected using the predicted elution time of the compound. A fraction collector may be used to collect the compound by turning on the fraction collector during the predicted elution time of the particular compound. The eluate is typically directed to a waste collector during all other periods.

In one embodiment, the compound of interest (or a portion of the compound) is collected without the use of an HPLC compatible detector using only the predicted elution time.

In another embodiment, the compound of interest (or a portion of the compound) is collected using the predicted elution time in combination with a signal from an HPLC compatible detector (such as, for example, a UV detector). The collector is turned on or activated when a peak is detected within the predicted elution time. It is important to note that a signal will only be sent to the fraction collector from the detector when a peak is detected within the predicted elution time of the compound of interest. The fraction collector is deactivated when the peak is no longer detected within the predicted elution time. Such a system may also use an algorithm designed to continue collection by the fraction collector outside of the predicted elution time until the peak has ended.

The present invention advantageously allows one or more compounds to be quickly and efficiently separated from one or more mixtures without having to generate and store a UV chromatogram from an initial analytical HPLC. That is, the present invention may be used to predict the elution time of a compound and collect the compound without the use of a UV chromatogram from the analytical HPLC column. However, such a chromatogram may be generated and used if desired.

EXAMPLES

The invention will be further explained by the following illustrative example that is intended to be non-limiting.

Example 1

A mixture (using dimethyl sulfoxide (DMSO) as the solvent) was provided that was expected to contain trifluralin with an expected mass of 335. A sample of the mixture (1 $\mu$L of 10 mg/mL) was introduced onto an analytical HPLC column including the following components: stationary phase-Ansys MetaChem Polaris C-18A 5 $\mu$; mobile phase-55% $CH_3OH$:45% $H_2O$ at time (t)=0 min, moving by gradient to 100% $CH_3OH$ at t=3 min, and remaining at 100% $CH_3OH$ until t=4 min; column length-50 mm; and column diameter-4.6 mm. The analytical HPLC was performed under ambient temperature at a flow rate of 1.5 mL/min.

A Thermo Finnigan AQA mass spectrometer was connected to the analytical HPLC column such that the eluate from the column flowed to the mass spectrometer. The mass spectrometer was calibrated to detect only the mass to charge ratio of 335±~3.0. The mass spectrometer was used to calculate the retention time of the compound by determining the time that the peak maximum of the mass to charge ratio appeared. FIG. 1 is a mass chromatogram of the time of the elution versus the relative abundance of the mass to charge ratio 335. As shown by the peak marked 335 in FIG. 1, the retention time of the compound was determined to be 3.3 min.

Next, the elution time of the compound from a preparative scale HPLC column was predicted. The elution time was predicted using a "correlation function" that is a linear correlation of retention time on the analytical HPLC column versus retention time on a preparative scale HPLC column. The correlation function was determined prior to the separation using a set of test compounds (i.e., the non-polar test mix) including acetophenone, benzene, toluene, and 2,6-dimethylnaphthalene. Each test compound was eluted using the analytical HPLC column discussed above and the preparative scale HPLC column discussed below. The results are shown in Table I below.

TABLE I

| Non-Polar Test Mix | | |
|---|---|---|
| Standard | PREPREP RT | PREP RT |
| acetophenone | 0.68 | 0.97 |
| benzene | 0.99 | 1.52 |
| toluene | 1.39 | 2.04 |
| 2-6-dimethylnaphthalene | 2.96 | 3.48 |

Figure 2:
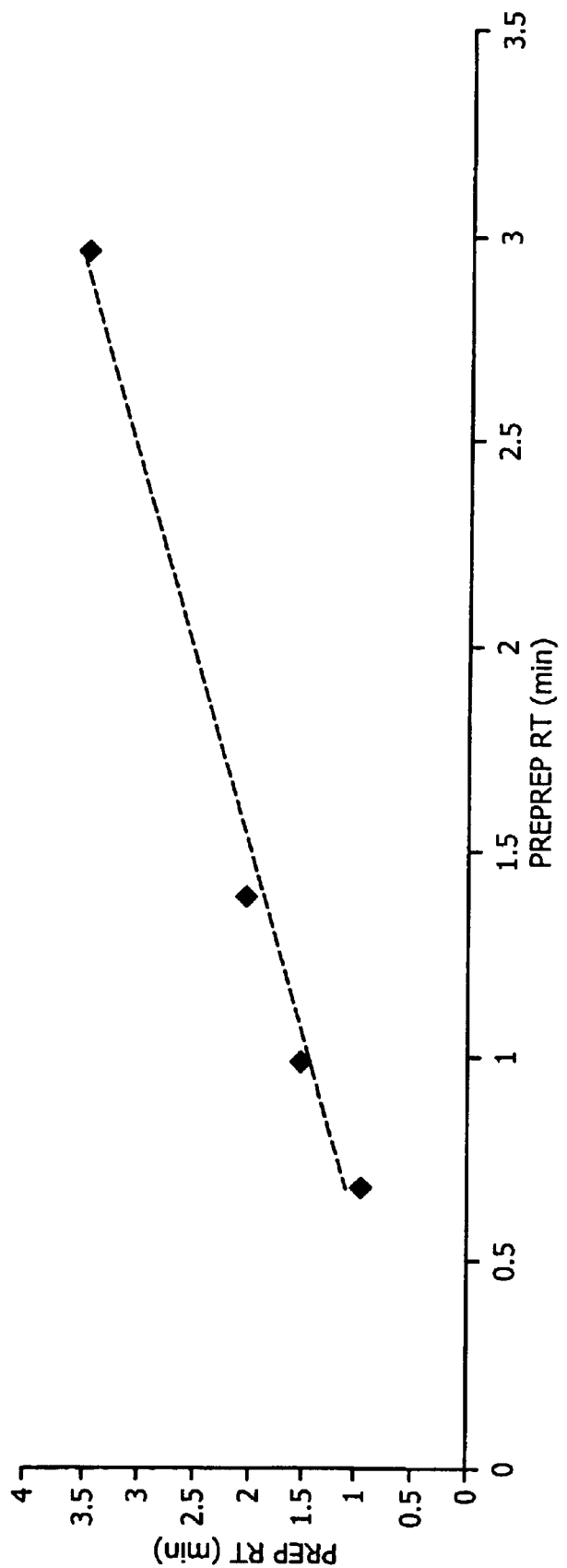
FIG. 2 is a graphical representation of a correlation function (obtained according to Example 1) of analytical HPLC retention time (i.e., PREPREP RT) versus preparative scale HPLC retention time (i.e., PREP RT).

The data of retention time on the analytical HPLC column (i.e., PREPREP RT) was plotted against the data of the retention time on the preparative scale HPLC column (i.e., PREP RT) to arrive at a linear correlation function (i.e., PREP RT=SLOPE×PREPREP RT+INTERCEPT). The correlation function that was determined follows: PREP RT=1.0552×PREPREP RT+0.4145. The correlation coefficient (i.e., $r^2$) was determined to be 0.9832. FIG. 2 illustrates the correlation function in graphical format. Using the correlation function, the predicted retention time of the trifluralin on the preparative scale HPLC column was determined to be 3.90 min. (i.e., 234 sec.). This predicted retention time was then used to determine a predicted elution time for the compound from the preparative scale HPLC column. A predicted elution time of ±20 sec. from the predicted retention time of 234 sec. was used to ensure that all or a majority of the compound peak was collected (i.e., the predicted elution time that was used was from 214 seconds to 254 seconds from introduction of the mixture onto the HPLC column).

The remaining mixture containing the compound was then subjected to a separation using a preparative scale HPLC column. The preparative scale HPLC column that was used contained the following components: stationary phase—Waters Xterra® Prep MS C18 5µ; mobile phase—50% $CH_3OH$:50% $H_2O$ at t=0 min, moving by gradient to 100% $CH_3OH$ at t=6.2 min; column length—50 mm; and column diameter—19 mm. The preparative scale HPLC was performed under ambient temperature at a flow rate of 28 mL/min.

Figure 3:
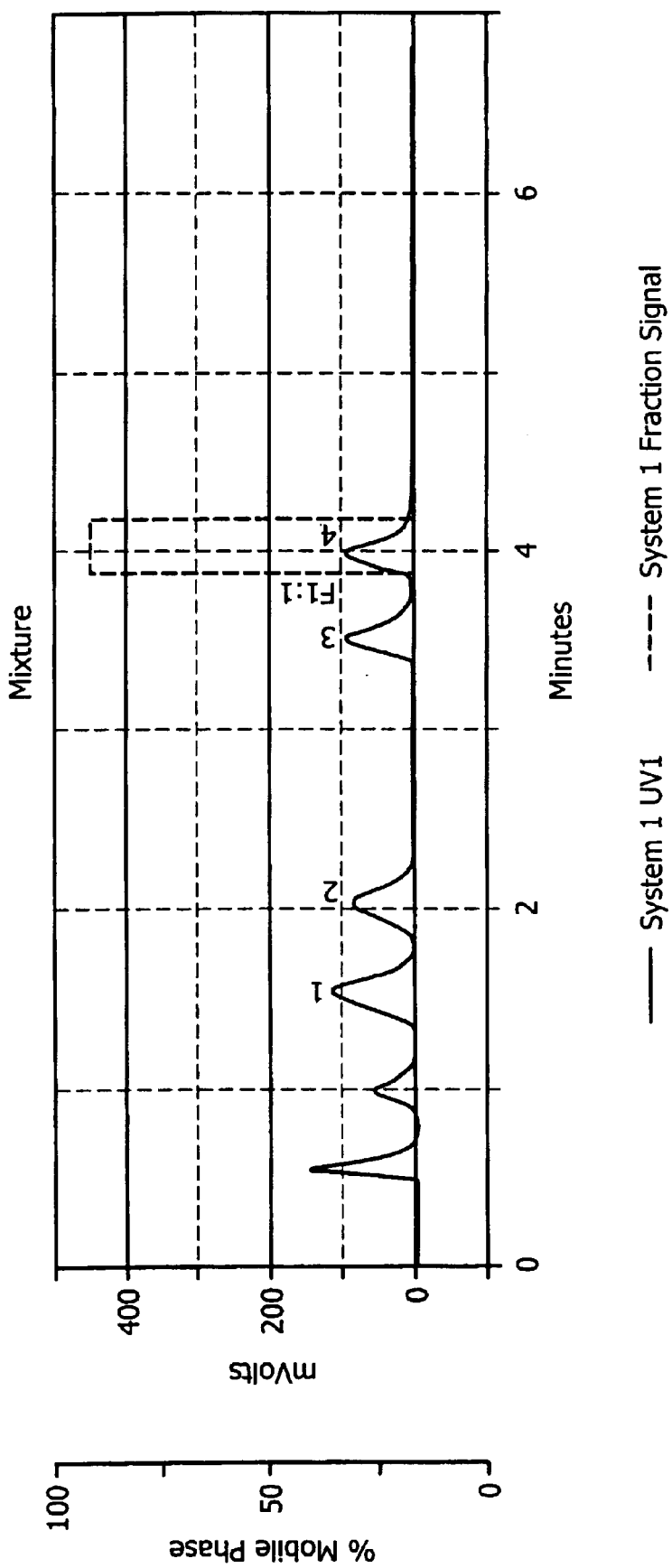
FIG. 3 is a UV chromatogram (obtained according to Example 1) illustrating the actual fraction collected on a preparative scale HPLC system within the predicted elution time.

A UV detector was connected to the preparative scale HPLC column capable of testing absorbance at a wavelength of 254 nm. An algorithm was used that was designed to begin collection only when a peak with a positive slope was detected within the predicted elution time. When a peak with a positive slope was detected by the UV detector during the predicted elution time, a signal was sent to a fraction collector connected to the column to direct the eluate to a collection vessel. The algorithm was also designed to end collection when the slope of the peak changed from a negative slope to zero or to a positive slope, and to begin collection again if another positive slope was detected. A UV chromatogram corresponding to the data from UV detector attached to the preparative scale HPLC is shown in FIG. 3 indicating the fraction collected within the predicted elution time (i.e., fraction F1:1).

While the invention has been described in detail and with reference to specific embodiments thereof, it will be apparent to one skilled in the art that various changes and modifications can be made without departing from the spirit and scope of the invention.

What is claimed is:

1. A method of separating a compound of interest from a mixture, the method comprising the steps of:
    (a) determining a static correlation function between retention time on an analytical HPLC column under a first set of conditions and retention time on a preparative scale HPLC column under a second set of conditions;
    (b) providing a mixture containing a compound of interest, the compound of interest having an expected mass;
    (c) subjecting a portion of the mixture to a separation using the analytical HPLC column under the first set of conditions to produce an eluate stream;
    (d) analyzing the eluate stream using a mass spectrometer to determine a retention time of the compound of interest on the analytical HPLC column;
    (e) predicting a retention time of the compound of interest on the preparative scale HPLC column using the static correlation function along with the determined retention time of the compound on the analytical HPLC column;
    (f) selecting a window of time around the predicted retention time within which the compound is expected to elute;
    (g) subjecting all or a portion of the remaining mixture to a separation using a preparative scale HPLC system comprising a preparative scale HPLC column, an HPLC compatible detector, and a fraction collector, the separation carried out under the second set of conditions; and
    (h) collecting at least a portion of the compound of interest using the fraction collector, the fraction collector being activated upon detection of a peak by the HPLC compatible detector within the selected window of time.

2. The method of claim 1 wherein the HPLC detector is selected from the group consisting of UV detector, ELSD, refractive index detector, and chemiluminescent nitrogen detector.

3. The method of claim 1 wherein data collected from the mass spectrometer consists essentially of the expected mass of the compound of interest and the retention time of the compound on the analytical HPLC column.

4. The method of claim 1 wherein a UV chromatogram is not generated from the separation using the analytical HPLC column.

5. The method of claim 1 wherein step (a) comprises determining the retention time of each of two or more test compounds on the analytical HPLC column under the first set of conditions and on the preperative HPLC column under the second set of conditions and correlating the retention times on the analytical HPLC column to the retention times on the preparative scale HPLC column.

6. A method of separating a compound of interest from a mixture, the method comprising the steps of:
    (a) determining a static correlation function between retention time on an analytical HPLC column under a first set of conditions and retention time on a preparative scale HPLC column under a second set of conditions;
    (b) providing a mixture containing a compound of interest, the compound of interest having an expected mass;
    (c) subjecting a portion of the mixture to a separation using the analytical HPLC column under the first set of conditions to produce an eluate stream;
    (d) analyzing the eluate stream using a mass spectrometer to determine a retention time of the compound of interest on the analytical HPLC column;
    (e) predicting an retention time for the compound of interest on the preparative scale HPLC column using the static correlation function along with the determined retention time of the compound on the analytical HPLC column;
    (f) selecting a window of time around the predicted retention time within which the compound is expected to elute;
    (g) subjecting all or a portion of the remaining mixture to a separation using a preparative scale HPLC system comprising a preparative scale HPLC column, the separation carried out under the second set of conditions; and
    (h) collecting at least a portion of the compound of interest using the selected window of time.

7. The method of claim 6 wherein the preparative scale HPLC system includes an HPLC compatible detector.

8. The method of claim 7 wherein the detector is selected from the group consisting of UV detector, ELSD, refractive index detector, and chemiluminescent nitrogen detector.

9. The method of claim 7 wherein the HPLC system includes a fraction collector that collects at least a portion of the compound of interest, the fraction collector being activated upon detection of a peak by the HPLC compatible detector within the predicted elution time.

10. The method of claim 6 wherein data collected from the mass spectrometer consists essentially of the expected mass of the compound of interest and the retention time of the compound on the analytical HPLC column.

11. The method of claim 6 wherein a UV chromatogram is not generated from the separation using the analytical HPLC column.

12. The method of claim 6 wherein the preparative scale HPLC system does not include an HPLC compatible detector.

13. The method of claim 6 wherein the collection step (h) is performed without the use of an HPLC compatible detector.

14. The method of claim 6 wherein step (a) comprises determining the retention time of each of two or test more compounds on the analytical HPLC column under the first set of conditions and on the preperative HPLC column under the second set of conditions and correlating the retention times on the analytical HPLC column to the retention times on the preparative scale HPLC column.

15. A method of separating compounds of interest present in a plurality of reaction product mixtures, the method comprising the steps of:

(a) determining a static correlation function between retention time on an analytical HPLC column under a first set of conditions and retention time on a preparative scale HPLC column under a second set of conditions;

(b) providing a plurality of reaction product mixtures, each mixture expected to contain a compound of interest having an expected mass;

(c) separately subjecting a portion of each reaction product mixture to a separation using the analytical HPLC column under the first set of conditions to produce a plurality of eluate streams;

(d) analyzing each eluate stream using a mass spectrometer to verify that the eluate stream contains a compound with an expected mass and to determine a retention time of each compound with an expected mass on the analytical HPLC column;

(e) predicting an retention time for each compound with an expected mass on the preparative scale HPLC column using the static correlation function along with the determined retention time of each compound on the analytical HPLC column;

(f) selecting a window of time around each predicted retention time within which each compound with an expected mass is expected to elute;

(g) separately subjecting all or a portion of each remaining mixture verified to contain a compound with the expected mass to a separation using a preparative scale HPLC system comprising a preparative scale HPLC column and a fraction collector, the separation carried out under the second set of conditions; and (h) separately collecting at least a portion of each compound verified to be present with the fraction collector using the selected window of time for each compound.

16. The method of claim 15 wherein at least two eluate streams produced in step (c) are combined for analysis in step (d) in a common mass spectrometer, the at least two eluate streams being chosen such that the expected compounds of interest in the streams have different expected masses that are distinguishable by mass spectrometry.

17. The method of claim 15 wherein at least two eluate streams produced in step (c) are combined for analysis in step (d) in a common mass spectrometer, at least one of the eluate streams being mechanically coded such that the expected compounds of interest in the streams are distinguishable by mass spectrometry.

18. The method of claim 15 further comprising determining the purity of the compound of interest immediately following the separation using the analytical HPLC column.

19. The method of claim 15 wherein the preparative scale HPLC system includes an HPLC compatible detector.

20. The method of claim 19 wherein the detector is selected from the group consisting of UV detector, ELSD, refractive index detector, and chemiluminescent nitrogen detector.

21. The method of claim 19 wherein the fraction collector is activated upon detection of a peak by the HPLC compatible detector within the selected window of time.

22. The method of claim 15 wherein a UV chromatogram is not generated from the separation using the analytical HPLC column.

23. The method of claim 15 wherein step (a) comprises determining the retention time of each of two or test more compounds on the analytical HPLC column under the first set of conditions and on the preperative HPLC column under the second set of conditions and correlating the retention times on the analytical HPLC column to the retention times on the preparative scale HPLC column.

\* \* \* \* \*

UNITED STATES PATENT AND TRADEMARK OFFICE
CERTIFICATE OF CORRECTION

PATENT NO. : 6,736,975 B2
DATED : May 18, 2004
INVENTOR(S) : Thierry Gandelheid et al.

It is certified that error appears in the above-identified patent and that said Letters Patent is hereby corrected as shown below:

Column 9,
Line 64, after "comprising" delete "a" and insert therefor -- the --.

Column 10,
Line 20, delete "preperative" and insert therefor -- preparative --.
Line 41, after "predicting" delete "an" and insert therefor -- a --.
Line 41, after "retention time" delete "for" and insert therefor -- of --.
Line 51, after "comprising" delete "a" and insert therefor -- the --.

Column 11,
Line 13, delete "test more" and insert therefor -- more test --.
Line 15, delete "preperative" and insert therefor -- preparative --.
Line 40, after "predicting" delete "an" and insert therefor -- a --.
Line 40, after "retention time" delete "for" and insert therefor -- of --.

Column 12,
Line 4, after "comprising" delete "a" and insert therefor -- the --.
Line 40, delete "test more" and insert therefor -- more test --.
Line 42, delete "preperative" and insert therefore -- preparative --.

Signed and Sealed this

Nineteenth Day of April, 2005

JON W. DUDAS
*Director of the United States Patent and Trademark Office*